United States Patent [19]

Kurashima et al.

[11] Patent Number: 4,654,428

[45] Date of Patent: Mar. 31, 1987

[54] PROCESS FOR PREPARATION OF SILICON-CONTAINING ISOCYANATE COMPOUNDS

[75] Inventors: Akira Kurashima; Akira Machiya, both of Aizuwakamatsu; Goichi Yamaguchi, Urawa, all of Japan

[73] Assignee: C. S. Kaseihin Company Inc., Tokyo, Japan

[21] Appl. No.: 810,314

[22] Filed: Dec. 17, 1985

[30] Foreign Application Priority Data

Dec. 18, 1984 [JP] Japan .................................. 59-265468
Jun. 17, 1985 [JP] Japan .................................. 60-129786

[51] Int. Cl.$^4$ ............................ C07F 7/10; C07F 7/18
[52] U.S. Cl. .................................................... 556/414
[58] Field of Search ........................................ 556/414

[56] References Cited

U.S. PATENT DOCUMENTS 3,584,024  6/1971  Pepe .................................... 556/414

FOREIGN PATENT DOCUMENTS 0374317  7/1973  U.S.S.R. ............................. 556/414

*Primary Examiner*—Paul F. Shaver
*Attorney, Agent, or Firm*—Michael N. Meller

[57] ABSTRACT

A silicon-containing isocyanate compound represented by the following general formula [I]:

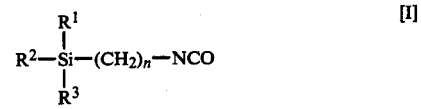

wherein each of $R^1$, $R^2$, and $R^3$ independently represents a hydrocarbon group having 1 to 10 carbon atoms, an alkoxy group having 1 to 6 carbon atoms or a trialkyl siloxy group (each alkyl having 1 to 4 carbon atoms), with the proviso that at least one of $R^1$, $R^2$, and $R^3$ is an alkoxy group having 1 to 6 carbon atoms, and n is a number of from 1 to 4, can be obtained in a high yield by reacting carbonyl chloride with a silicon-containing alkylamine represented by the following general formula [II]:

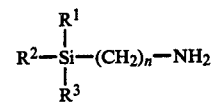

wherein $R^1$, $R^2$, $R^3$, and n are as defined above, in an inert organic solvent in the presence of a tertiary amine. If a filtrate remaining after removal of a tertiary amine hydrochloride from the reaction liquid, a liquid remaining after removal of the solvent from the filtrate, or a distillate formed by distillation of this liquid is treated with an alkali metal salt or alkaline earth metal salt of higher fatty acid or an aromatic carboxylic acid, the intended product can be obtained at a high purity in a high yield.

10 Claims, No Drawings

PROCESS FOR PREPARATION OF SILICON-CONTAINING ISOCYANATE COMPOUNDS

BACKGROUND OF THE INVENTION (1) Field of the Invention

The present invention relates to a process for the preparation of silicon-containing isocyanate compounds. More particularly, it relates to a process for the preparation of a silylalkyl isocyanate compound having an alkoxy-silicon linkage, which is valuable as the starting material for the production of various silyl group-containing compounds.

(2) Description of the Related Art

As an example of the process for the production of a silicon compound as described above, a process is known in which a corresponding alkoxysilane and allyl isocyanate are subjected to addition reaction at a high temperature in the presence of rhodium trichloride to prepare an alkoxysilylpropyl isocyanate (see Japanese Examined Patent Publication No. 55-40,592). This process, however, has problems in that the catalyst used is expensive, the reaction must be carried out at a high temperature, and the product is limited to a silylpropyl isocyanate.

As other examples, there are known a process in which a corresponding silylalkylamine is converted to a halosilyl ester of carbamic acid and the ester then decomposed (see U.S. Pat. No. 4,064,151) and a process in which a corresponding silylalkylamine is converted to a methyl ester of carbamic acid and the ester then thermally decomposed in vacuum (see U.S. Pat. No. 3,494,951). In these processes, however, since the starting material is first converted to a carbamate and the carbamate then decomposed, the number of steps in the process is increased. Moreover, the manufacturing cost is increased by using the starting material in the form of a carbamate ester, or by the recovery thereof. Especially, in the latter process, since heating is conducted at a high temperature in vacuum, the reaction apparatus becomes complicated and the equipment cost is increased.

Therefore, the industrial production of an isocyanate compound has been generally carried out through a reaction between an amine and carbonyl chloride.

However, in the conventional reaction between a silylalkyl amine having an alkoxy-silicon linkage and carbonyl chloride, the alkoxy group is preferentially chlorinated and the intended product cannot be obtained (see Example 1 of Japanese Examined Patent Publication No. 42-23,171).

Furthermore, in the reaction between an aminoalkyldisiloxane (free of an alkoxy group) and carbonyl chloride, only a two-stage process is known in which a trimethylsilyl group is first introduced into the amino group (see French Pat. No. 1,563,380).

SUMMARY OF THE INVENTION

It is a primary object of the present invention to provide a process in which an intended isocyanate compound is prepared advantageously while controlling side reactions.

In accordance with the present invention, there is provided a process for the preparation of silicon-containing isocyanate compounds represented by the following general formula [I]:

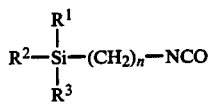

wherein each of $R^1$, $R^2$, and $R^3$ independently represents a hydrocarbon group having 1 to 10 carbon atoms, an alkoxy group having 1 to 6 carbon atoms or a trialkyl siloxy group (each alkyl having 1 to 4 carbon atoms), with the proviso that at least one of $R^1$, $R^2$, and $R^3$ is an alkoxy group having 1 to 6 carbon atoms, and n is a number of from 1 to 4, which comprises reacting carbonyl chloride with a silicon-containing alkylamine represented by the following formula [II]:

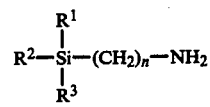

wherein $R^1$, $R^2$, $R^3$ and n are as defined above, in an inert organic solvent in the presence of a tertiary amine.

DESCRIPTION OF THE PREFERRED EMBODIMENTS

As the tertiary amine used in the present invention, there can be mentioned aliphatic tertiary amines such as trimethylamine, triethylamine, and tripropylamine; aromatic tertiary amines such as N,N-dimethylaniline and N,N-diethylaniline; and heterocyclic tertiary amines such as pyridine, picoline, and lutidine.

In the silicon-containing alkylamine compound represented by the general formula [II], $R^1$, $R^2$, and $R^3$ are selected from alkyl groups such as methyl, ethyl, propyl, butyl, and hexyl groups; aryl groups such as a phenyl group; aralkyl groups such as a benzyl group; alkenyl groups such as vinyl and allyl groups; alkoxy groups such as methoxy and ethoxy groups; and trialkyl siloxy groups such as trimethylsiloxy and triethylsiloxy groups. However, at least one of $R^1$, $R^2$, and $R^3$ should be an alkoxy group. As specific examples of the compound represented by the general formula [II], there can be mentioned α-dimethoxymethylsilylmethylamine, α-diethoxymethylsilylmethylamine, γ-trimethoxysilylpropylamine, γ-triethoxysilylpropylamine, γ-methyldimethoxysilylpropylamine, γ-methyldiethoxysilylpropylamine, γ-tributoxysilylpropylamine, δ-dimethylmethoxysilylbutylamine, and γ-diethoxy(trimethylsiloxy)silylpropylamine.

Ordinarily, carbonyl chloride and the silicon-containing alkylamine represented by the general formula (II) are used at a molar ratio of about 1:1, but an excessive amount of carbonyl chloride may be used according to need.

It is preferred that the tertiary amine be used in an amount of 1.5 to 3 moles per mole of the silicon-containing alkylamine represented by the general formula [II]. If the amount of the tertiary amine is too small and below this range, undesirable side reactions will take place.

Any organic solvent inactive to the reactants and product can be used as the solvent in the present invention. For example, hydrocarbons such as benzene, toluene, n-hexane, and cyclohexane; halogenated hydrocarbons such as methylene chloride, chloroform, and trichloroethylene; ethers such as ethyl ether and dioxane;

and mixtures of two or more thereof are preferably used.

The reaction is accomplished by dropping a mixed solution of the silicon-containing alkylamine represented by the general formula (II) and the tertiary amine in the above-mentioned organic solvent into a solution formed by dissolving carbonyl chloride in the above-mentioned organic solvent. The reaction is carried out preferably at a temperature of $-50°$ C. to $+50°$ C., especially $-30°$ C. to $+10°$ C. After completion of the reaction, the crystal of the hydrochloride of the tertiary amine is separated from the reaction liquid by filtration, and the intended product is isolated from the filtrate.

Isolation of the intended product can be accomplished by distillation of the filtrate, but in a product isolated only through distillation will include a minute amount of a tertiary amine hydrochloride dissolved in the filtrate and/or hydrogen chloride formed by dissociation or the like. Therefore, if the product is stored for a long time, for example, more than one week, a change in the product readily occurs with the elapse of time and the product becomes opaque.

To obviate this disadvantage, it is preferred that the filtrate remaining after removal of the tertiary amine hydrochloride from the reaction liquid, the liquid remaining after removal of the solvent from the above filtrate, or a distillate formed by distillation of this liquid, be treated with an alkali metal or alkaline earth metal salt of at least one carboxylic acid selected from the group consisting of unsaturated fatty acids having 8 to 18 carbon atoms, saturated fatty acids having 8 to 18 carbon atoms, and aromatic carboxylic acids having 7 to 15 carbon atoms. An intended isocyanate compound having a high purity can be stably obtained by adopting the step of treatment with the alkali metal or alkaline earth metal salt of the carboxylic acid. Note, the purity and stability can be further increased if the pH value is adjusted to 6 to 7 after this treatment and purification is effected by distillation.

As the carboxylic acid component in the alkali metal or alkaline earth metal salt of the carboxylic acid, there can be mentioned higher saturated fatty acids such as caprylic acid, lauric acid, myristic acid, and stearic acid; unsaturated fatty acids such as oleic acid and sorbic acid; and aromatic carboxylic acids such as benzoic acid and phthalic acid.

As the alkali metal or alkaline earth metal, there can be mentioned Na, K, Mg, Ca, and Ba.

It is preferred that the alkali metal or alkaline earth metal salt of the carboxylic acid be used in an amount equal to or larger than an amount equivalent to hydrogen chloride present in the intended product.

The preferred treatment procedures are as follows.

An alkali metal or alkaline metal salt of a carboxylic acid as mentioned above is added to any filtrate remaining after removal of the tertiary amine hydrochloride from the reaction liquid, the liquid remaining after removal of the solvent from the above filtrate, and the distillate formed by distillation of the above liquid. The mixture is then sufficiently stirred and the pH value is adjusted to 6 to 7. The precipitated carboxylic acid, alkali metal or alkaline earth metal chloride and/or excessive alkali metal or alkaline earth metal salt of the carboxylic acid is removed by filtration, and the filtrate is preferably subjected to distillation.

Since the intended product of the process of the present invention has an isocyanate group and an alkoxy group in combination, it is valuable for use in various fields, for example, as a coupling agent for glass fibers or polyester films and a coating agent for resins.

The present invention will now be described in detail with reference to the following examples that by no means limit the scope of the invention.

EXAMPLE 1

In 150 ml of toluene was dissolved 9.9 g of carbonyl chloride, and a solution of 22.1 g of γ-triethoxysilylpropylamine and 27.9 g of N,N-dimethylaniline in 50 ml of toluene was dropped into the above solution at $-5°$ C. to $-10°$ C. over a period of 3 hours to effect reaction. After the reaction, the crystal of N,N-dimethylaniline chloride was removed by filtration and the filtrate was subjected to distillation to recover toluene, whereby 19.8 g of γ-triethoxysilylpropyl isocyanate was obtained as a fraction having a boiling point of 88° C. to 91° C. under 4.5 mmHg.

When 2 g of calcium stearate was added to the thus-obtained product and the mixture was stirred for 4 hours, the pH value became 7. Excessive calcium stearate and the precipitate were removed by filtration, and when the filtrate was distilled, 17.8 g of γ-triethoxysilylpropyl isocyanate was obtained as a fraction having a boiling point of 87° to 89° C. under 4 mmHg.

Where calcium stearate was not added, the product became opaque when stored for 1 week. In contrast, the treated product remained stable for a storage period of 6 months.

As another purification method, 4.0 g of sodium myristate was added instead of calcium stearate to the liquid remaining after the recovery of the toluene, and the mixture was stirred until the pH value became 7. Excessive sodium myristate and the precipitate were recovered by filtration and the filtrate was subjected to distillation, whereby 18.8 g of γ-triethoxysilylpropyl isocyanate was obtained as a fraction having a boiling point of 93° C. to 95° C. under 6 mmHg. The product remained stable and unchanged, even when stored for more than 6 months.

As still another purification method, 18.0 g of sodium stearate was added to the filtrate remaining after the removal of N,N-dimethylaniline hydrochloride and the mixture was stirred until the pH value became 7. Excessive sodium stearate and the precipitate were recovered by filtration and the filtrate was distilled to obtain 18.9 g of γ-triethoxysilylpropyl isocyanate as a fraction having a boiling point of 81° C. to 83° C. under 3 mmHg. The product remained stable and did not become opaque, even when stored for more than 6 months.

EXAMPLE 2

In 150 ml of toluene was dissolved 9.9 g of carbonyl chloride, and a solution of 22.1 g of γ-triethoxysilylpropylamine and 23.3 g of triethylamine in 50 ml of toluene was dropped into the above solution at 0° C. to $-5°$ C. over a period of 3 hours to effect reaction. After the reaction, the crystal of triethylamine hydrochloride was recovered by filtration and the filtrate was distilled to recover toluene, whereby 16.0 g of γ-triethoxysilylpropyl isocyanate was obtained at a fraction having a boiling point of 88° C. to 91° C. under 4.5 mmHg.

EXAMPLE 3

In 150 ml of toluene was dissolved 9.9 g of carbonyl chloride, and a solution of 19.1 g of γ-diethoxymethylsilylpropylamine and 24.2 g of N,N-dimethylaniline in 50 ml of toluene was dropped into the above solution at −5° C. to −10° C. over a period of 3 hours to effect reaction. After the reaction, the crystal of dimethylaniline hydrochloride was removed by filtration and toluene was recovered from the filtrate, a fraction having a boiling point of 80° C. to 85° C. under 6 mmHg was collected, and 6.3 g of calcium sorbate was added to this fraction. The mixture was stirred for 3 hours and the liquid was distilled to recover 17.6 g of γ-diethoxymethylsilylpropyl isocyanate as a fraction having a boiling point of 82° C. to 85° C. under 6 mmHg. The product remained stable, even when stored for more than 6 months.

EXAMPLE 4

In 150 ml of methylene chloride was dissolved 9.9 g of carbonyl chloride, and a solution of 19.1 g of γ-diethoxymethylsilylpropylamine and 23.3 g of triethylamine in 50 ml of methylene chloride was dropped into the above solution at −5° C. to −10° C. over a period of 3 hours to effect reaction. After the reaction, the crystal of triethylamine hydrochloride was removed by filtration and the filtrate was distilled to recover methylene chloride, whereby 17.4 g of γ-diethoxymethylsilylpropyl isocyanate was recovered as a fraction having a boiling point of 91° C. to 93° C. under 9 mmHg.

As another purification method, after methylene chloride was recovered from the filtrate remaining after removal of the crystal of triethylamine hydrochloride by filtration, a fraction having a boiling point of 91° C. to 93° C. under 9 mmHg was collected, and 9 g of sodium oleate was added to the fraction. The mixture was then stirred for 20 minutes and, the pH value became 7. Excessive sodium oleate and the precipitate were removed by filtration, and the filtrate was distilled to obtain 15.7 g of γ-diethoxymethylsilylpropyl isocyanate as a fraction having a boiling point of 80° C. to 82° C. under 5 mmHg. The product remained stable, even when stored for more than 6 months.

EXAMPLE 5

In 150 ml of toluene was dissolved 9.9 g of carbonyl chloride, and a solution of 29.5 g of γ-diethoxy(trimethylsiloxy)silylpropylamine and 23.3 g of triethylamine in 50 ml of toluene was dropped into the above solution at −5° C. to −10° C. over a period of 3 hours to effect reaction. After the reaction, the crystal of triethylamine hydrochloride was removed by filtration and the filtrate was distilled to recover toluene, whereby 24.0 g of γ-diethoxy(trimethylsiloxy)silylpropyl isocyanate was obtained as a fraction having a boiling point of 93° C. to 94° C. under 12 mmHg.

The above mentioned procedure was repeated wherein, after toluene was recovered from the filtrate remaining after removal of the crystal of triethylamine hydrochloride, 4.5 g of sodium caprylate was added to the liquid. The mixture was then stirred for 20 minutes and the pH value became 7. Excessive sodium caprylate and the precipitate were removed by filtration and the filtrate was distilled to obtain 21.5 g of γ-diethoxy(trimethylsiloxy)silylpropyl isocyanate as a fraction having a boiling point of 84° C. to 86° C. under 8 mmHg. The product remained stable, even when stored for more than 6 months.

EXAMPLE 6

In 150 ml of ethyl ether was dissolved 9.9 g of carbonyl chloride, and a solution of 22.1 g of γ-triethoxysilylpropylamine and 18.2 g of pyridine in 50 ml of ethyl ether was dropped into the above solution at −5° C. to −10° C. over a period of 3 hours to effect reaction. After the reaction, the crystal of pyridine hydrochloride was removed by filtration and the filtrate was distilled to recover ethyl ether, whereby 17.3 g of γ-triethoxysilylpropyl isocyanate was obtained as a fraction having a boiling point of 95° C. to 100° C. under 8 mmHg.

When 1.2 g of barium stearate was added to the thus-obtained product and the mixture stirred for 3 hours, the pH value became 7. Excessive barium stearate and the precipitate were removed by filtration and the filtrate was distilled to obtain 15.9 g of γ-triethoxysilylpropyl isocyanate as a fraction having a boiling point of 90° C. to 93° C. under 5 mmHg. The purity of the product was 99% and the product remained stable for a long period of time.

EXAMPLE 7

In 150 ml of toluene was dissolved 9.9 g of carbonyl chloride, and a solution of 16.3 g of α-diethoxymethylsilylmethylamine and 24.2 g of N,N-dimethylaniline in 50 ml of toluene was dropped into the above solution at −5° C. to −10° C. over a period of 3 hours to effect reaction. After the reaction, the crystal of N,N-dimethylaniline hydrochloride was removed by filtration, and the filtrate was distilled to recover toluene, whereby 13.0 g of α-diethoxymethylsilylmethyl isocyanate was obtained as a fraction having a boiling point of 196° C. to 198° C.

The above-mentioned procedure was repeated wherein 3.9 g of sodium caprate was added to the above residue remaining after the recovery of toluene. The mixture was then stirred for 20 minutes and the pH value became 7. Excessive sodium caprate and the precipitate were removed by filtration and the filtrate was distilled to obtain 11.0 g of α-diethoxymethylsilylmethyl isocyanate as a fraction having a boiling point of 86° C. to 88° C. under 20 mmHg. The product remained stable, even when stored for more than 6 months.

EXAMPLE 8

In 150 ml of toluene was dissolved 9.9 g of carbonyl chloride, and a solution of 14.5 g of δ-dimethylmethoxysilylbutylamine and 27.9 g of N,N-dimethylaniline in 50 ml of toluene was dropped into the above solution at −5° C. to −10° C. over a period of 3 hours to effect reaction. After the reaction, the crystal of N,N-dimethylaniline hydrochloride was removed by distillation and the filtrate was distilled to recover toluene, whereby 12.8 g of δ-dimethylmethoxysilylbutyl isocyanate was obtained as a fraction having a boiling point of 95° C. to 100° C. under 12 mmHg.

Then, 1 g of magnesium stearate was added to the thus-obtained product. The mixture was then stirred and the pH value became 7. Excessive magnesium stearate and the precipitate were removed by filtration, and the filtrate was distilled to obtain 11.5 g of δ-dimethylmethoxysilylbutyl isocyanate as a fraction having a boiling point of 98° C. to 100° C. under 12 mmHg. The product remained stable, even when stored for more than 6 months.

EXAMPLE 9

In 150 ml of toluene was dissolved 9.9 g of carbonyl chloride, and a solution of 19.1 g of γ-diethoxymethylsilylpropylamine and 24.2 g of N,N-dimethylaniline in 50 ml of toluene was dropped into the above solution at −5° C. to −10° C. over a period of 3 hours to effect reaction. After the reaction, N,N-dimethylaniline hydrochloride was removed by filtration, the filtrate was distilled to recover toluene, and a fraction having a boiling point of 91° C. to 93° C. under 9 mmHg was collected. Then, 1 g of sodium benzoate was added to the fraction. The mixture was then stirred for 3 hours and the pH value became 7. Excessive sodium benzoate and the precipitate were removed by filtration, and the filtrate was distilled to obtain 15.6 g of γ-diethoxymethylsilylpropyl isocyanate as a fraction having a boiling point of 80° C. to 82° C. under 5 mmHg. The product remained stable, even when stored for more than 6 months.

EXAMPLE 10

In 150 ml of toluene was dissolved 9.9 g of carbonyl chloride, and a solution of 19.1 g of γ-diethoxymethylsilylpropylamine and 24.2 g of N,N-dimethylaniline in 50 ml of toluene was dropped into the above solution at −5° C. to −10° C. over a period of 3 hours to effect reaction. After the reaction, N,N-dimethylaniline hydrochloride was removed by filtration and toluene was recovered from the filtrate, and a fraction having a boiling point of 91° C. to 93° C. under 9 mmHg was collected. Then, 0.8 g of dipotassium phthalate was added to the fraction. The mixture was then stirred for 3 hours and the pH value became 7. Excessive dipotassium phthalate and the precipitate were removed by filtration, and the filtrate was distilled to 15.6 g of γ-diethoxymethylsilylpropyl isocyanate as a fraction having a boiling point of 80° C. to 82° C. under 5 mmHg. The product remained stable, even when stored for more than 6 months.

We claim:

1. A process for the preparation of silicon-containing isocyanate compound represented by the following general formula [I]:

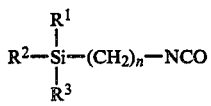

wherein each of $R^1$, $R^2$, and $R^3$ independently represents a hydrocarbon group having 1 to 10 carbon atoms, an alkoxy group having 1 to 6 carbon atoms or a trialkyl siloxy group (each alkyl having 1 to 4 carbon atoms), with the proviso that at least one of $R^1$, $R^2$, and $R^3$ is an alkoxy group having 1 to 6 carbon atoms, and n is a number of from 1 to 4, which comprises reacting carbonyl chloride with a silicon-containing alkylamine represented by the following formula [I]:

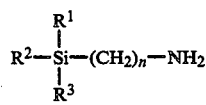

wherein $R^1$, $R^2$, $R^3$, and n are as defined above, in an inert organic solvent in the presence of a tertiary amine.

2. A process according to claim 1, wherein the silicon-containing alkylamine represented by the general formula [II] and carbonyl chloride are used at a molar ratio of about 1:1.

3. A process according to claim 1, wherein the tertiary amine is used in an amount of 1.5 to 3 moles per mole of the silicon-containing alkylamine represented by the general formula [II].

4. A process according to claim 1, wherein the silicon-containing alkylamine represented by the general formula [II] is at least one member selected from the group consisting of α-dimethoxymethylsilylmethylamine, α-diethoxymethylsilylmethylamine, γ-trimethoxysilylpropylamine, γ-triethoxysilylpropylamine, γ-methyldimethoxysilylpropylamine, γ-methyldiethoxysilylpropylamine, γ-tributoxysilylpropylamine, δ-dimethylmethoxysilylbutylamine, and γ-diethoxy(trimethylsiloxy)silylpropylamine.

5. A process according to claim 1, wherein the inert organic solvent is selected from the group consisting of hydrocarbons, halogenated hydrocarbons, and ethers.

6. A process according to claim 1, wherein the reaction is carried out at a temperature of −50° C. to +50° C.

7. A process according to claim 1, which further comprises the steps of:

treating a filtrate remaining after removal of a tertiaryamine hydrochloride from the reaction liquid containing the silicon-containing isocyanate represented by the general formula [I], a liquid remaining after removal of the solvent, or a distillate formed by distillation of said liquid, with an alkali metal salt or alkaline earth metal salt of at least one carboxylic acid selected from the group consisting of saturated and unsaturated fatty acids having 8 to 18 carbon atoms and aromatic carboxylic acids having 7 to 15 carbon atoms, and recovering the silicon-containing isocyanate compound represented by the general formula [I] at a high purity from the treated product.

8. A process according to claim 7, wherein the amount of the alkali metal salt or alkaline earth metal salt of the carboxylic acid is equal to or larger than an amount equivalent to hydrogen chloride present in the reaction product liquid to be treated.

9. A process according to claim 7, wherein the alkali metal salt or alkaline earth metal salt of the carboxylic acid is a sodium, potassium, magnesium, calcium or barium salt of at least one carboxylic acid selected from the group consisting of caprylic acid, lauric acid, myristic acid, stearic acid, oleic acid, sorbic acid, benzoic acid, and phthalic acid.

10. A process according to claim 7, wherein at the treatment with the alkali metal salt or alkaline earth metal salt of the carboxylic acid, said metal salt is added to the reaction product liquid to be treated, and after the pH value of the liquid mixture becomes 6 to 7, the precipitated carboxylic acid, alkali metal or alkaline metal chloride and the excessive alkali metal salt or alkaline earth metal salt of the carboxylic acid are removed by filtration and the silicon-containing isocyanate compound represented by the general formula is recovered by distillation of the filtrate.

* * * * *